US00PP30551P3

(12) United States Plant Patent
Silverstein et al.

(10) Patent No.: US PP30,551 P3
(45) Date of Patent: Jun. 4, 2019

(54) APPLE TREE NAMED 'YCP'

(50) Latin Name: *Malus domestica*
Varietal Denomination: YCP

(71) Applicants: Maurice Silverstein, Orrvale (AU); Catherine Silverstein, Orrvale (AU); Bo Silverstein, Orrvale (AU)

(72) Inventors: Maurice Silverstein, Orrvale (AU); Catherine Silverstein, Orrvale (AU); Bo Silverstein, Orrvale (AU)

( * ) Notice: Subject to any disclaimer, the term of this patent is extended or adjusted under 35 U.S.C. 154(b) by 14 days.

(21) Appl. No.: 15/731,687

(22) Filed: Jul. 17, 2017

(65) Prior Publication Data

US 2018/0027710 P1 Jan. 25, 2018

(30) Foreign Application Priority Data

Jul. 19, 2016 (AU) ..... 2016/190

(51) Int. Cl.
*A01H 5/08* (2018.01)
*A01H 6/74* (2018.01)

(52) U.S. Cl.
USPC ..... Plt./172
CPC ..... *A01H 6/7418* (2018.05); *A01H 5/08* (2013.01)

(58) Field of Classification Search
USPC ..... Plt./156, 161, 172
See application file for complete search history.

(56) References Cited

U.S. PATENT DOCUMENTS

| | | | |
|---|---|---|---|
| PP7,880 | P | 6/1992 | Cripps |
| PP16,725 | P2 | 6/2006 | Staples et al. |
| PP18,660 | P2 | 3/2008 | Tuite |
| PP21,606 | P3 | 1/2011 | Barnsby |
| PP27,187 | P3 | 9/2016 | Francis |

*Primary Examiner* — Susan McCormick Ewoldt
*Assistant Examiner* — Karen M Redden
(74) *Attorney, Agent, or Firm* — Phase M Legal

(57) ABSTRACT

A new and distinct apple tree *Malus domestica* named 'YCP'. 'YCP' is a spontaneous limb mutation of the variety 'Cripps Pink' and is distinguished by its bright lime green fruit color, its Yellow-green one-year old shoots, its petals of white-only color, and its pedicel, sepals and balloon blossom all of Yellow-green color.

7 Drawing Sheets

Latin name of the genus and species:
Botanical classification: *Malus domestica.*
Variety denomination: The new apple tree variety denomination is 'YCP'.

BACKGROUND OF THE VARIETY:

The present invention is a new and distinct cultivar of apple tree botanically known as *Malus domestica* and referred to by the cultivar name 'YCP'. 'YCP' was discovered as a spontaneous limb mutation in a commercial orchard of the variety 'Cripps Pink' (U.S. Plant Pat. No. 7,880).

'YCP' was first observed in 2009 in Shepparton East, Victoria, Australia, where it was distinguished by its bright lime green fruit color. 'YCP' is also distinguished from its parent by its lime green current season wood growth on both sunny side and shaded side and its lack of red anthocyanin on the back of the leaf petiole and its lack of red anthocyanin during all stages of blossom where the balloon blossom and petals are lime green in color. Asexual reproduction of 'YCP' was carried out by bud grafting in 2011 and trees of 'YCP' were planted for additional observation at Shepparton East, Victoria, Australia. 'YCP' has since been fruited through successive asexually propagated generations at Shepparton East and has been observed to remain true to type with the distinguishing characteristics retained through successive generations of asexual reproduction.

BRIEF DESCRIPTION OF THE VARIETY

'YCP' is primarily distinguished by its lime green fruit color and lack of red anthocyanin color in the wood and leaf petiole and balloon blossom and petals during all stages of flowering. These and other distinguishing characteristics are set forth in the tables below. Under similar growing conditions in Tasmania, Australia, under commercial practice, 'YCP' is distinguishable from its parent 'Cripps Pink' as described in Table 1 below:

TABLE 1

Comparison of 'YCP' to 'Cripps Pink'

| Characteristic | 'Cripps Pink' | 'YCP' |
|---|---|---|
| 1 Year Old Shoot: Sun Exposed Side Color | Greyed-orange 165C | Yellow-green 152A |
| 1 Year Old Shoot: Shaded Side Color | Green-brown 199B | Yellow-green 152A |
| Petals: Color Lower Surface | Red-purple 61B | White NN155C |
| Pedicel: Sun Exposed Side Color | Red-purple 59A | Yellow-green 144C |
| Pedicel: Shaded Side Color | Yellow-green 144B | Yellow-green 144C |
| Petals: Sepals | Yellow-green 144B with Red-Purple 59A on tip | Yellow-green 144C |

TABLE 1-continued

Comparison of 'YCP' to 'Cripps Pink'

| Characteristic | 'Cripps Pink' | 'YCP' |
|---|---|---|
| Petals: Balloon Blossom Color | Red-purple 73B | Yellow-green 144C |
| Petals: Tight Bud Stage Color | Red-purple 67B | Yellow-green 144C |

'YCP' is also distinguishable from the similar green-yellow commercial variety 'Golden Delicious' (unpatented), which is a parent variety of 'Cripps Pink', as shown in Table 2 below:

TABLE 2

Comparison of 'YCP' to 'Golden Delicious' a parent of 'Cripps Pink'

| Characteristic | 'Golden Delicious' | 'YCP' |
|---|---|---|
| 1 Year Old Shoot: Sun Exposed Side Color | Greyed-purple N186C | Yellow-green 152A |
| 1 Year Old Shoot: Shaded Side Color | Yellow-green 152B | Yellow-green 152A |
| Petals: Color Lower Surface | Red-purple 61B | White NN155C |
| Pedicel: Sun Exposed Side Color | Red-purple 59A | Yellow-green 144C |
| Pedicel: Shaded Side Color | Yellow-green 144B | Yellow-green 144C |
| Petals: Sepals | Yellow-green 144B with Red-Purple 59A on tip | Yellow-green 144C |
| Petals: Balloon Blossom Color | Red-purple 73B | Yellow-green 144C |
| Petals: Tight Bud Stage Color | Red-purple 67B | Yellow-green 144C |
| Fruit at Harvest: Sun Exposed Side | Green-yellow 1B with Red 39B Blush from Sun | Yellow-green 150C - No Pink/Red Blush from Sun observed |
| Petiole: Extent of Anthocyanin | Petiole Anthocyanin is 5.2 mm on average Red-purple 60A. Balance of Petiole is Yellow-green N144C | Petiole is all Yellow-green 151A No Anthocyanin present in any leaf Petiole |
| Harvest Date - Time of Eating | Early to Mid-Season, Mar. 5, 2017 in Tasmania, Australia | Mid to Late season, Mar. 31, 2017 in Tasmania, Australia |
| Date of Full Bloom | 28th of October in Tasmania, Australia | 15th of October in Tasmania, Australia |

BRIEF DESCRIPTION OF THE PHOTOGRAPHS

Typical specimens of the tree and blossoms for the new apple tree variety 'YCP' are shown in the accompanying photographs. The colors shown are as true as possible within the usual limits of this kind of illustration.

DETAILED BOTANICAL DESCRIPTION OF THE VARIETY

Figure 1:
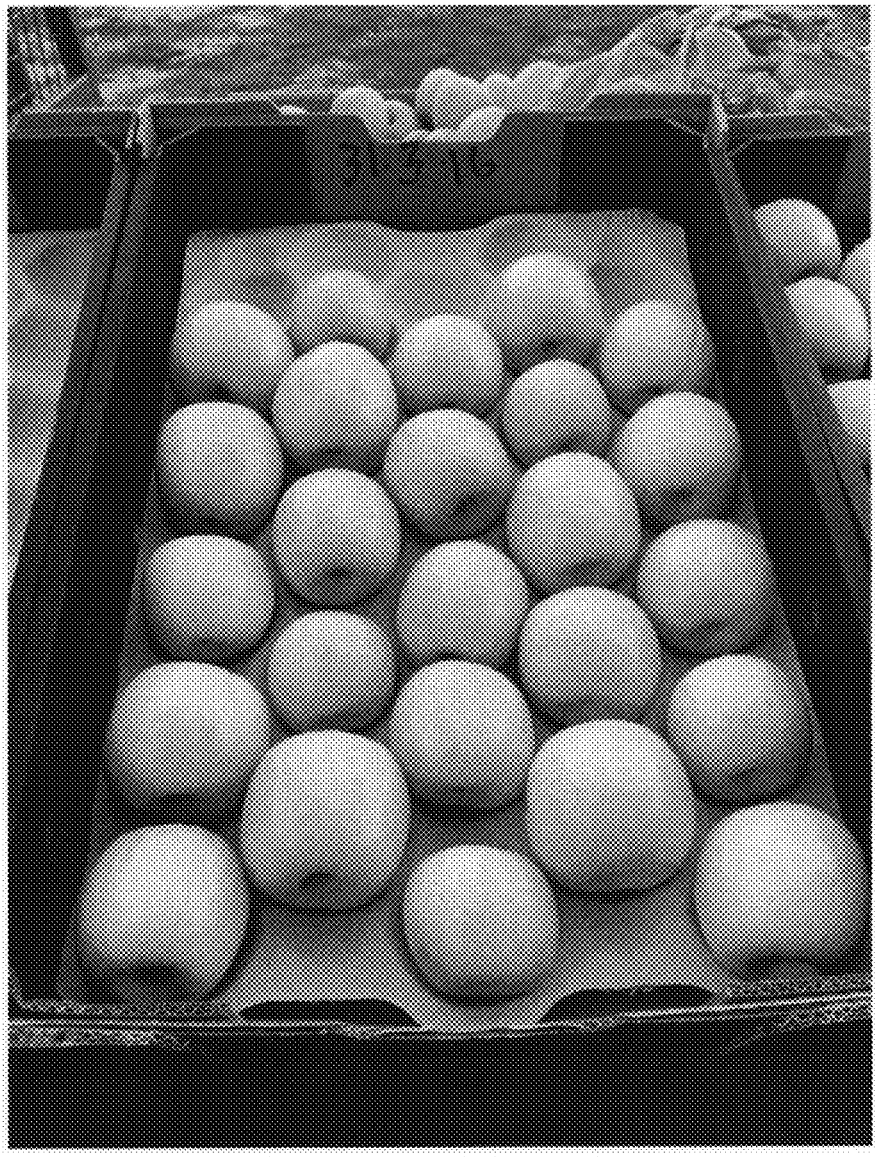
FIG. 1 shows current season's fresh fruit of 'YCP' harvested at maturity.
Figure 2:
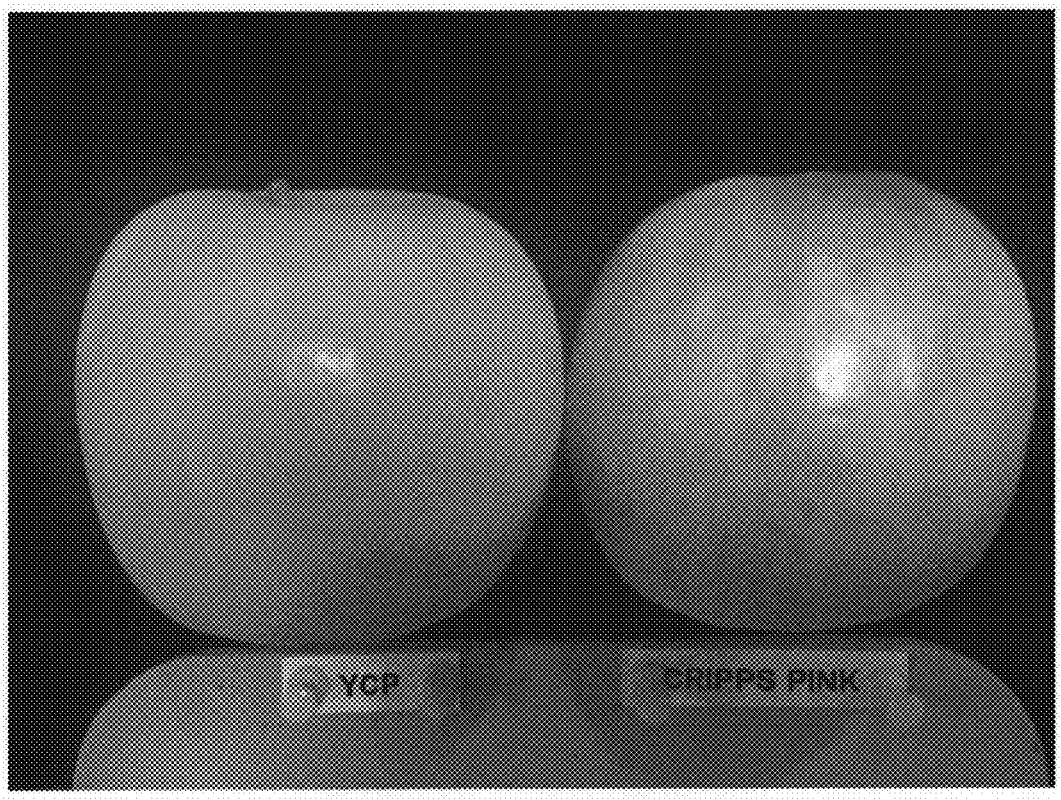
FIG. 2 shows current season's fresh fruit of 'YCP' (on the left) compared to fruit of 'Cripps Pink' (on the right), both harvested at maturity.
Figure 3:
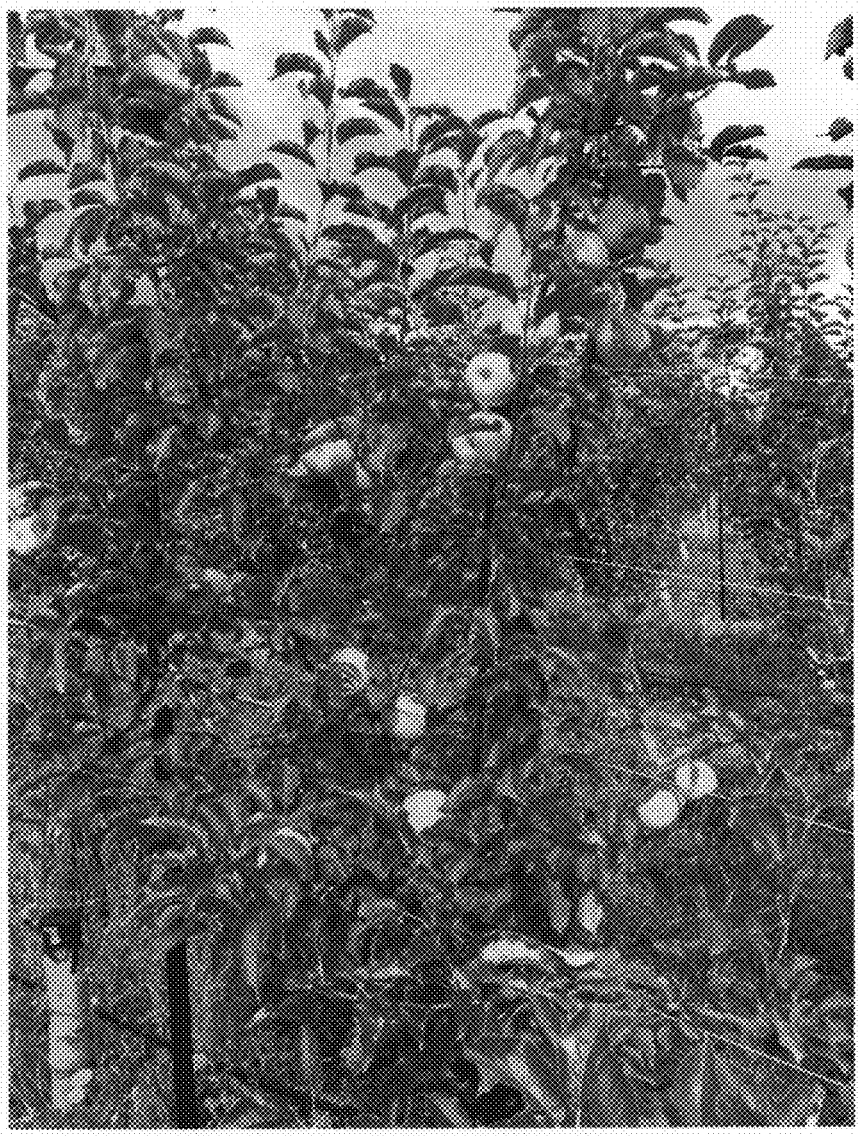
FIG. 3 shows a tree of 'YCP' in its third growing season on 'MM106' rootstock.
Figure 4:
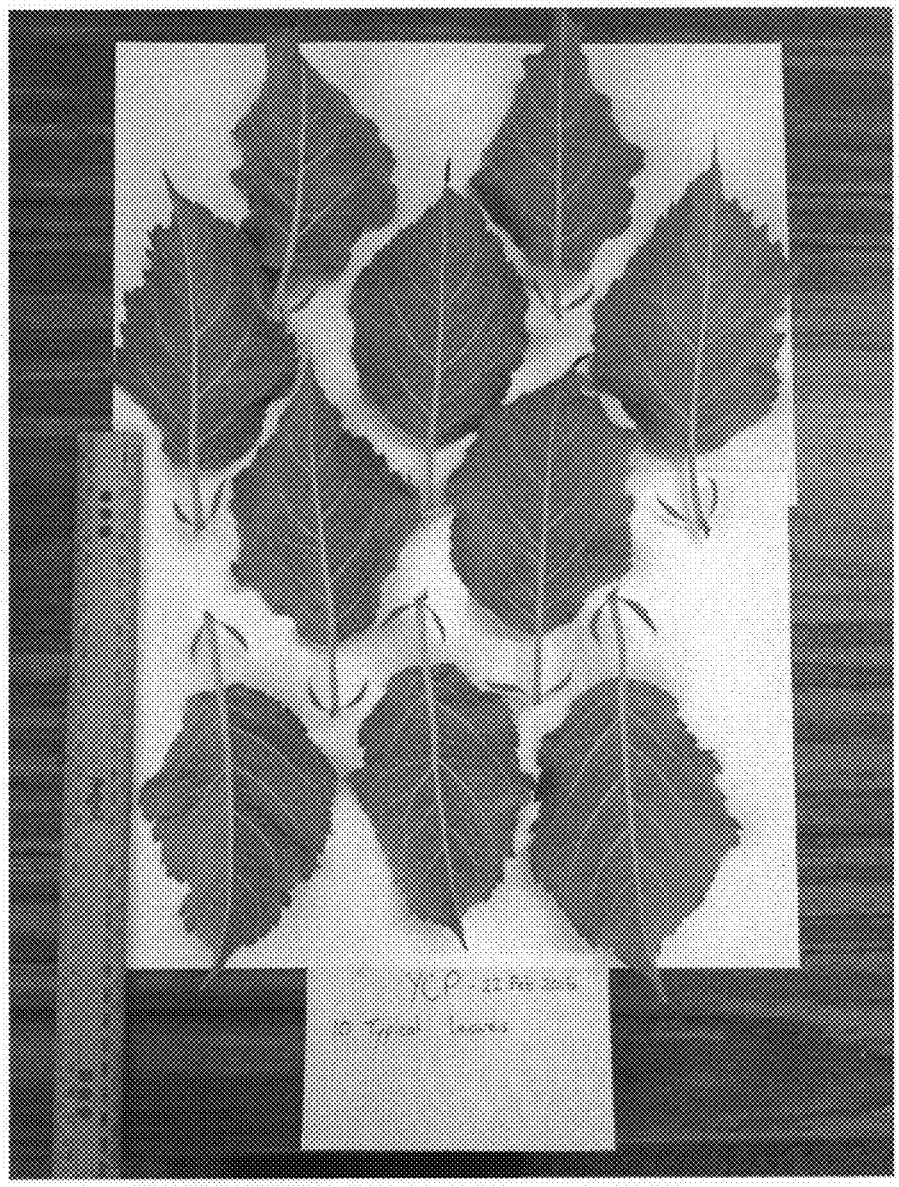
FIG. 4 shows the underside of the leaves of a 3-year-old current season's shoot of 'YCP' in its third growing season on 'MM106' rootstock.
Figure 5:
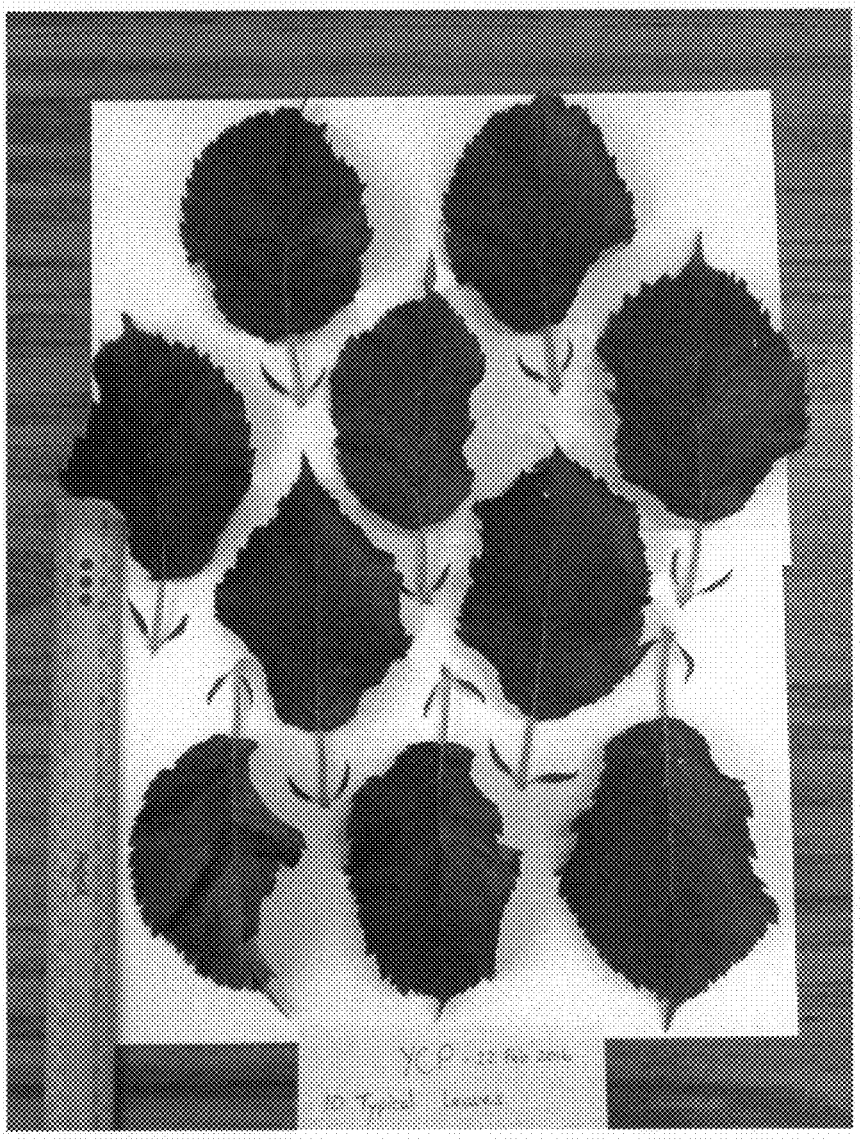
FIG. 5 shows the upper side of the leaves of a 3-year-old current season's shoot of 'YCP' in its third growing season on 'MM106' rootstock.
Figure 6:
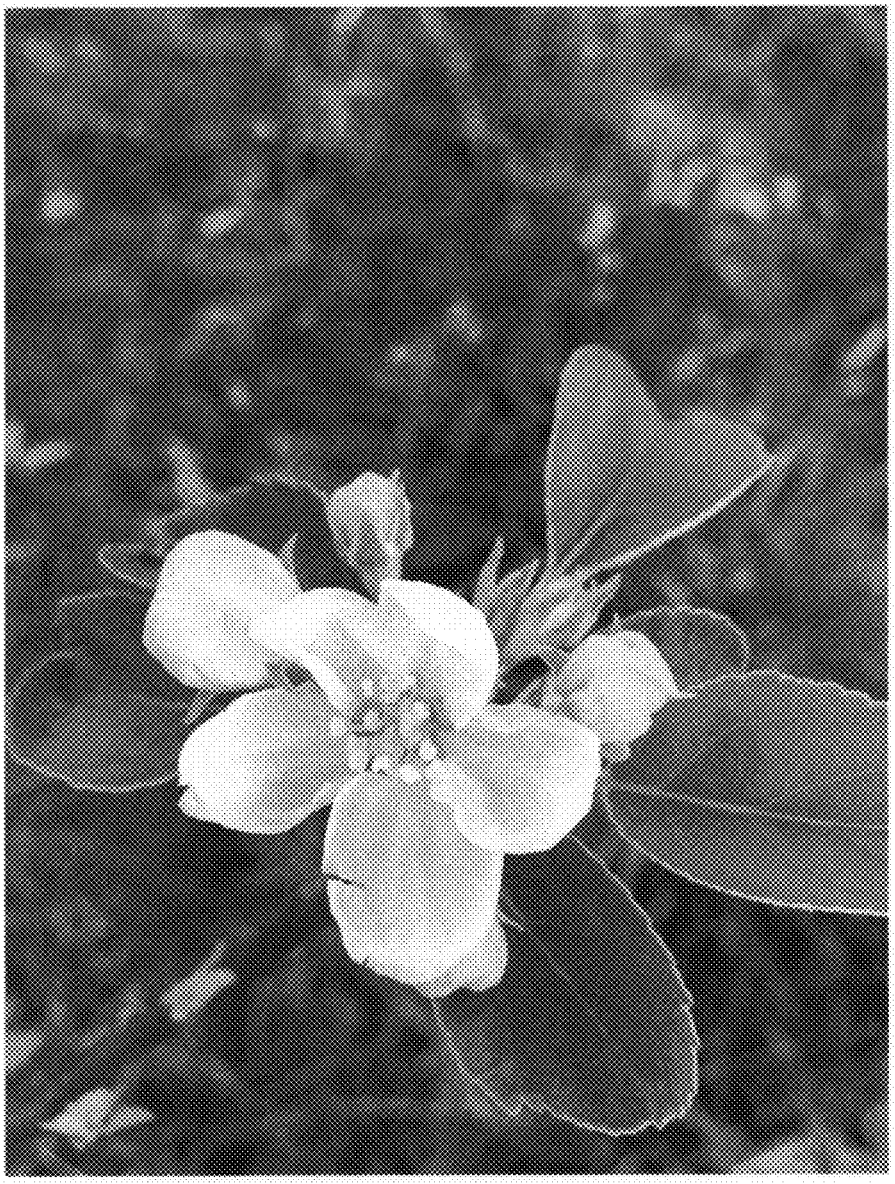
FIG. 6 shows a blossom of 'YCP' on a 'YCP' tree in its third growing season on 'MM106' rootstock; and, FIG. 7 shows fruit of 'YCP' on a 'YCP' tree in its third growing season on 'MM106' rootstock.
Figure 7:
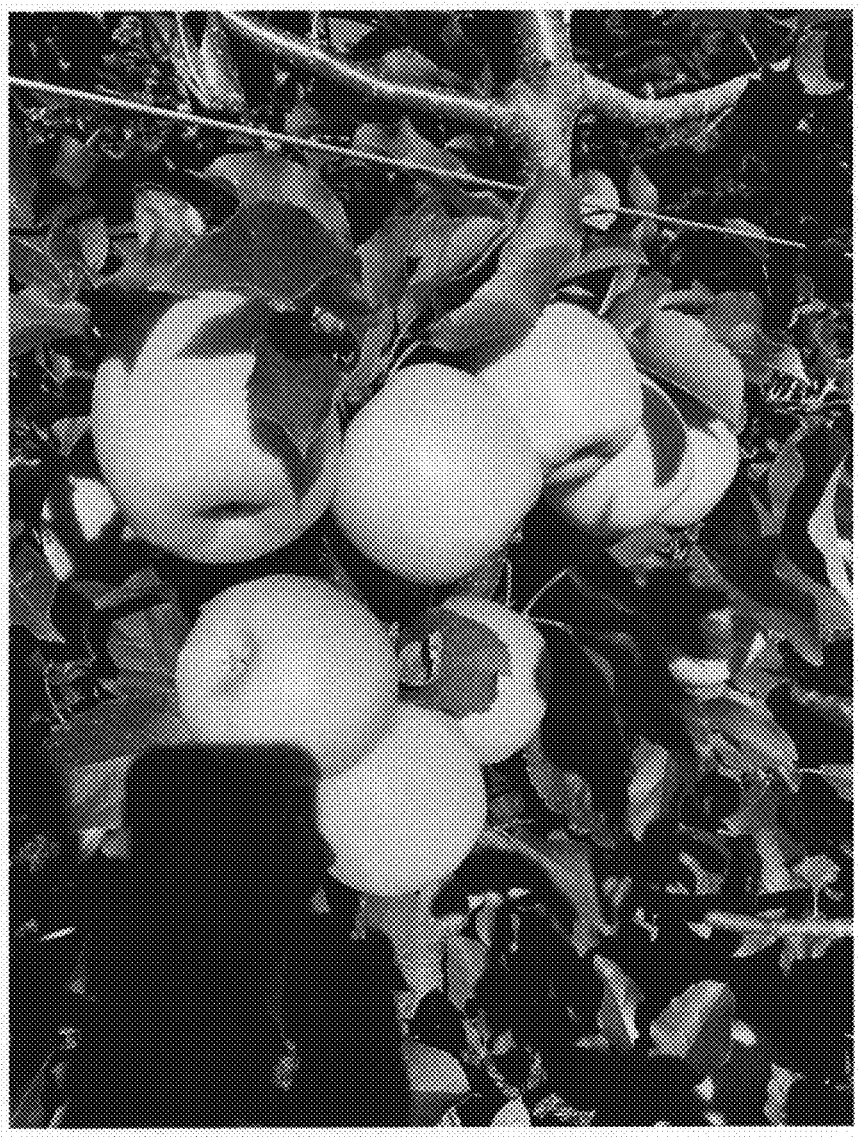

The following-detailed botanical description is based on observations made during the third growing season at Lucaston, Tasmania, Australia of 3-year-old trees planted on 'MM106' rootstock (unpatented). 'YCP' is a spontaneous limb mutation of the variety 'Cripps Pink' and is distinguished by its bright lime green fruit color, its yellow-green one-year old shoots, its petals of white-only color, and its pedicel, sepals and balloon blossom all of yellow-green color. The cultivar has not been observed under all possible environmental conditions. The phenotype may vary significantly with variations in the environment such as temperature, length of day and light intensity, without any variance in genotype. It should be understood that the characteristics described will vary somewhat depending upon cultural practices and climatic conditions, and will vary with location and season. The plant and flower quantified measurements and foliage size are expressed as an average of measurements taken from several individual plants of 'YCP' using standard commercial cultural practices. The measurements of any individual plant or any group of plants of 'YCP' may vary from the stated average. All colors are described according to The Royal Horticultural Society Colour Chart ($5^{TH}$ edition 2007).

Tree:

*Vigor.*—Strong.

*Type.*—Ramified — Bearing on Spurs and Long Shoots.

*Habit.*—Spreading to Upright.

*Height.*—3.6 m.

*Trunk diameter.*—51 mm at 100 mm above the graft.

*Bark texture.*—Smooth with some ridging.

*Bark color.*—Yellow-green 152A on both sides.

*Branch.*—Fruiting branches located at around 700 mm above the graft union.

*Length.*—2 m average.

*Diameter.*—26 mm at base.

*Crotch angle.*—Branches on unpruned tree are horizontal to 10 degrees and occasionally upright.

*Bark color.*—Yellow-green 152A on sun exposed side and Yellow-green 152A on shaded side.

*Lenticel length.*—0.5 to 1 mm Average.

*Lenticel color.*—Yellow-orange 15C.

*Quantity of lenticels per cm$^2$.*—7 to 9 per cm$^2$.

One year old shoot:

*Length.*—900 mm average.

*Color.*—Yellow-green 152A on sun exposed side and Yellow-green 152A on shaded side.

*Pubescence.*—Medium to Strong.

*Thickness.*—7 mm average.

*Internode length.*—30 mm average.

*Number of lenticels per cm$^2$.*—7 to 9 per cm$^2$.

Flowers:

*Diameter of fully open flower.*—45.3 mm.

*Relative position of petal margin.*—Free to touching.

*Quantity of flowers per cluster.*—5 to 7.

*Date of beginning of flowering.*—$5^{th}$ of October in Tasmania.

*Date of full bloom.*—15th of October in Tasmania.
*Pollination requirement.*—Pollination required by another diploid variety flowering at similar time.

Petals:
*Quantity per flower.*—5.
*Shape.*—Ovate to ellipsoid.
*Length.*—20.5 mm.
*Width.*—14.5 mm.
*Apex.*—Ovoid.
*Base.*—Cuneate to obovate at base.
*Margin.*—Smooth.
*Color.*—Upper surface — White NN155C.
*Color.*—Lower surface — White NN155C.
*Pistils.*—15 mm long; 45A Yellow-green Color.
*Stigma.*—0.6 mm diameter; 45A Yellow-green Color.
*Position of stigma relative to anther.*—Same level.
*Style.*—5 fused at base; Length 10.45 mm; Color is 145A Yellow-green; Pubescent at base.
*Ovary.*—Pubescent; 3.5 mm average diameter; Color Yellow-green 144B.
*Anthers.*—21 average per flower; Length 2.2 mm; Width 1.76 mm; Ample pollen quantity, 10B Yellow Color.
*Pedicel.*—Length 33 mm average; Diameter 1.89 mm; Color: 144C Yellow-green on sun exposed side; 144C Yellow-green on shaded side.
*Sepals.*—Quantity 5; Length 8.2 mm average; Color: 144C Yellow-green from base to tip with smooth straight margin and pubescent.

Leaves:
*Length.*—96.9 mm average.
*Width.*—73.4 mm average.
*Length/width ratio.*—1.3:1.
*Blade margin.*—Bicrenate.
*Shape.*—Oval to obtuse.
*Apex.*—Acute in shape
*Base.*—Obtuse in shape.
*Pubescence.*—Description: Lightly pubescent on underside.
*Color.*—Upper surface — Green 137A.
*Color.*—Lower surface — Yellow-green 146C.
*Attitude in relation to shoot.*—Outward.
*Petiole.*—Length 27.3 mm; Diameter 2.8 mm; Color: Yellow-green 151A.

Fruit:
*Quantity per cluster.*—5 to 7 per cluster if no thinning occurs.
*Diameter.*—77.5 mm average.
*Height.*—75 mm average.
*Ratio of height to width.*—About 1:0.97.
*General shape in profile.*—Cylindrical and slightly ellipsoid at base.
*Position of maximum diameter.*—Near center.
*Ribbing.*—Moderate.
*Crowning at calyx end.*—Moderate.
*Size of eye.*—9.06 mm average.
*Aperture of eye.*—Mostly closed, occasionally open.
*Length of sepal.*—6 mm average length.
*Bloom of skin.*—Absent or weak.
*Greasiness of skin.*—Absent or weak.
*Background color of skin.*—Yellow-green 150C.
*Amount of over color.*—None.
*Over color of skin.*—None.
*Intensity of over color.*—None.
*Pattern of over color.*—None.
*Amount of russet around stalk cavity.*—Absent.
*Amount of russet on cheeks.*—Absent.
*Area of russet around eye basin.*—Absent.
*Length of stalk.*—13.9 mm average.
*Thickness of stalk.*—2.4 mm average.
*Stalk color.*—Greyed-orange 164B.
*Depth of stalk cavity.*—14.3 mm average.
*Width of stalk cavity.*—31.1 mm average.
*Depth of eye basin.*—8.4 mm average.
*Width of eye basin.*—31 mm average.
*Flesh color.*—Yellow 11D.
*Firmness of flesh.*—9.25 kg, Firm.
*Flesh texture.*—Firm and crisp.
*Aroma.*—Fresh.
*Juiciness.*—Ample.
*Total soluble solids.*—14.6° Brix.
*Seeds.*—Minimum of 1, mostly 2 per cell; 9 per fruit; Acute; Greyed-orange 167B; Aperture of locules closed or slightly open.

Harvest:
*Harvest date.*—Time of Eating Maturity — Mid to Late season, Mar. 31, 2017 in Tasmania, Australia.
*Number of picks.*—One.
*Yield.*—15 kg from typical three-year-old tree.
*Disease/insect resistance/susceptibility.*—No resistance/susceptibility noted. Winter hardiness, cold tolerance, drought and heat tolerance are similar to parent variety. No unusual hardiness or tolerance noted.

Market use: Fresh.

We claim:

1. A new and distinct apple tree substantially as described and illustrated herein.

* * * * *